United States Patent [19]

Heemels

[11] Patent Number: 6,055,454
[45] Date of Patent: Apr. 25, 2000

[54] CARDIAC PACEMAKER WITH AUTOMATIC RESPONSE OPTIMIZATION OF A PHYSIOLOGIC SENSOR BASED ON A SECOND SENSOR

[75] Inventor: Jan Pieter Heemels, Oudergem, Belgium

[73] Assignee: Cardiac Pacemakers, Inc., St. Paul, Minn.

[21] Appl. No.: 09/122,466

[22] Filed: Jul. 27, 1998

[51] Int. Cl.[7] .............................. A61N 1/365; A61N 1/362
[52] U.S. Cl. ................................................. 607/18; 607/19
[58] Field of Search ........................................ 607/18, 19

[56] References Cited

U.S. PATENT DOCUMENTS

| | | |
|---|---|---|
| 4,782,836 | 11/1988 | Alt ............................................. 607/19 |
| 4,905,697 | 3/1990 | Heggs et al. ............................... 607/18 |
| 4,926,863 | 5/1990 | Alt .............................................. 607/19 |
| 5,101,824 | 4/1992 | Lekholm .................................... 607/18 |
| 5,441,524 | 8/1995 | Rueter et al. .............................. 607/18 |
| 5,514,162 | 5/1996 | Bornzin et al. ............................ 607/19 |
| 5,755,740 | 5/1998 | Nappholz .................................. 607/18 |

*Primary Examiner*—William E. Kamm
*Assistant Examiner*—Carl H. Layno
*Attorney, Agent, or Firm*—Nikolai, Mersereau & Dietz, P.A.

[57] ABSTRACT

A rate adaptive cardiac pacemaker having a first sensor for measuring a physiologic parameter reflecting metabolic demand and a second sensor for measuring a parameter reflecting the physical motion or activity of the patient, wherein the second sensor is used to generate a dynamic target pacing rate which the first sensor is optimized to over time, thereby reducing the time constant for the adaptation of the first sensor and minimizing the amount of clinical time required to initialize the cardiac pacemaker.

7 Claims, 3 Drawing Sheets

CARDIAC PACEMAKER WITH AUTOMATIC RESPONSE OPTIMIZATION OF A PHYSIOLOGIC SENSOR BASED ON A SECOND SENSOR

BACKGROUND OF THE INVENTION

1. Field of the Invention

The present invention relates generally to an implantable cardiac stimulating apparatus. More particularly, the present invention relates to a rate adaptive cardiac rhythm management device having a first sensor for measuring a physiologic parameter reflecting metabolic demand and a second sensor for measuring a parameter reflecting the physical motion or activity of the patient, wherein the second sensor is used to generate a dynamic target pacing rate which the first sensor is optimized to over time, thereby reducing the time constant for the adaptation of the first sensor and minimizing the amount of clinical time required to initialize the cardiac rhythm management device.

2. Discussion of the Prior Art

A cardiac rhythm management device, or cardiac pacemaker, may be generalized as an implantable instrument designed to supplant some or all of an abnormal heart's natural pacing functions. Early attempts at cardiac rhythm management devices involved fixed-rate pacing where electrical stimulation signals are delivered to myocardial tissue at fixed intervals in order to ensure proper heart function. Although generally effective, this technique is nonetheless disadvantageous in that it does not allow the cardiac pacemaker to vary the rate of the electrical stimulation signals in response to variations in metabolic activity, such as during periods of rest or exercise, thereby resulting in a heart rate which is either too fast or slow relative to the metabolic needs of the patient. To overcome these deficiencies, a whole class of "rate adaptive" cardiac pacemakers have been developed that operate to sense some parameter correlating with metabolic need and then, using the sensed signal, derive a rate-controlling index for adjusting the pacing rate between a minimum or lower rate limit and a maximum or upper rate limit.

Physiologic parameters that are most commonly employed in rate-adaptive pacing may include any number of parameters indicative of metabolic demand, such as blood Ph, blood temperature, QT interval, pre-ejection interval, stroke volume, blood oxygen saturation, respiratory rate, and minute ventilation. A problem exists, however, in that these physiologic parameters respond relatively slowly to changes in the patient's level of exercise and, thus, can cause to patient to experience a hemodynamic deficiency due to the lag time between the onset of a new level of exercise and the reaction thereto by the pacemaker. In an effort to achieve a more rapid response to metabolic demand, various cardiac rhythm management devices have been developed which include a second sensing element for detecting the physical activity of the patient under the theory that motion or physical activity is directly correlative to the sinus rate of the patient and will thus allow the cardiac pacemaker to be more responsive to true metabolic demand.

U.S. Pat. No. 4,782,836 to Alt discloses one such dual-sensor rate-adaptive pacemaker, employing an activity sensor in conjunction with a blood temperature sensor wherein one of two algorithms is employed for relating blood temperature to pacing rate depending upon the level of patient exercise as detected by the activity sensor. U.S. Pat. No. 4,860,751 to Callaghan teaches yet another dual-sensor rate-adaptive pacemaker characterized in that the output of the activity sensor is utilized by control circuitry to enable the physiological sensor to monitor a selected physiologic parameter only if the physical activity of the patient exceeds a predetermined threshold. U.S. Pat. No. 4,905,697 to Heggs discloses the use of a blood temperature sensor for increasing the pacing rate of a pacemaker due to exercise and a motion sensor to trigger a decrease in the pacing rate following cessation of exercise. U.S. Pat. No. 4,926,863 to Alt teaches the use of an accelerometer for detecting the activity of the patient and a blood temperature sensor for detecting metabolic demand, wherein the accelerometer converts mechanical movement of the patient to a corresponding electrical signal which is combined with the sensed blood temperature parameter signal to confirm the metabolic state of the patient. U.S. Pat. No. 5,101,824 to Lekholm discloses a rate-adaptive pacemaker having two or more sensors for sensing physiologic parameters and patient activity, wherein an addressable rate matrix is employed to produce a specific pacing rate unique to each combination of sensor inputs.

The foregoing prior art references, however, all suffer a significant drawback in terms of the initialization process performed following the implantation of the cardiac pacemaker. The process of initialization involves having the physician set or program the cardiac pacemaker such that the sensors are appropriately tuned or optimized to allow the cardiac pacemaker to accurately respond to changes in the patient's metabolic demand. The algorithms used to control physiologic sensors typically have relatively long time constants of up to 30 minutes or more. The lengthy time constant is disadvantageous, however, in that it consumes a substantial amount of clinical time in order to effectuate the initialization. As will be appreciated, this is also costly and disadvantageous in that it effectively limits the number of patients whose pacemakers may be initialized within a given period of time so as to negatively impact the efficiency of the clinical operations. Invariably, physicians end up bypassing the lengthy automatic initialization process by manually setting the response slope of the physiologic sensor in an effort to send the patients home shortly after a post-implantation follow-up examination. Manual optimization of the sensors is disadvantageous in that it is typically based on "best guess" approximation which, of course, is highly subjective and more likely to result in non-optimal sensor rate settings.

Still further drawbacks exist with regard to the algorithms employed to adapt the physiologic and activity sensors. These algorithms, typically referred to as "automatic slope algorithms," are used to adapt a sensor response based on a feedback mechanism. One common feedback mechanism is dependent upon whether the pacing rate achieves a maximum sensor rate (MSR) within a predetermined time period. MSR is defined as the maximum pacing rate allowed as a result of sensor control and is typically programmed from 50–185 pulses per minute (ppm) in 5-ppm increments. Another common feedback mechanism is dependent upon whether the pacing rate achieves a sensor rate target (SRT) which is lower than the MSR within a predetermined time period. Algorithms of the first type are known to result in inappropriate response optimization in that it assumes that the patient exercises up to the programmed MSR in every time period. Algorithms of the second type require programming of a patient individual TSR which can be described as the typical maximum daily achieved rate. However, this is an arbitrary procedure since the physician will typically rely on subjective patient data to program this rate. Furthermore, both types of algorithms have very long time constants for optimization typically measured in months. This is disadvantageous, once again, in that it is contrary to the physician's goal of sending the patient home with an optimized response. Another disadvantage with these algorithms is that they typically result in extremely aggressive sensor response after a period of sedentary behavior or immobility.

A need therefore exists for an improved cardiac pacemaker with automatic response optimization of a physiologic sensor based on an activity sensor which overcomes the aforementioned deficiencies in the prior art.

OBJECTS AND SUMMARY OF THE INVENTION

The rate-adaptive cardiac pacemaker constructed in accordance with the present invention includes a pacemaker housing adapted to be implanted subcutaneously in the chest area and suitably electrically connected to the heart. The cardiac pacemaker includes a first sensor for measuring a physiologic parameter reflecting metabolic demand and a second sensor, e.g., a motion sensor for measuring a parameter reflecting the physical motion or activity of the patient. The second sensor is used to generate a dynamic target pacing rate and the first sensor is optimized to the dynamic target rate over time so as to reduce the time constant for the adaptation of the first sensor and to minimize the amount of clinical time required to initialize the cardiac pacemaker and to avoid aggressive response after a sedentary period.

The first sensor may be configured to sense any of a variety of physiologic parameters indicative of metabolic demand, such as blood Ph, blood temperature, QT interval, pre-ejection interval, stroke volume, blood oxygen saturation, respiratory rate, and minute ventilation. In a preferred embodiment, the first sensor is employed to detect minute ventilation. This may be accomplished by positioning a stimulating tip electrode on the distal end of the lead contained within the heart, positioning a more proximally located electrode in the form of a metal ring disposed on the lead body, and supplying an alternating current drive signal between the lead's tip ring electrode and the pacemaker's metal housing. The drive signal has a frequency and amplitude which is sufficiently low to preclude capture. The ring or tip electrode on the lead and an indifferent electrode disposed on the pacemaker's header or the metal housing socket are connected to a sense amplifier. Breathing activity as well as systolic events and other motion artifacts combine to modulate the alternating current carrier signal. The modulated carrier is fed into a demodulator whose output is an analog representation of the envelope which remains when the carrier is removed. An analog-to-digital converter may then be provided which functions to sample the analog signal at a predetermined frequency and which then provides at its output a serial signal train of digital pulses which define the amplitude of the analog input at the sampling time. The digital signal train can then be applied as an input to a four-pole elliptic filter and decameter circuit. The use of the adaptive filter also allows a peak detection algorithm to be used in determining tidal volume and ventilatory rate. The minute ventilation is, of course, the product of those two indices. While minute ventilation is a good candidate as a parameter indicative of metabolic demand, those skilled in the art are aware of various others that can be readily sensed by the "first sensor" and limitation to minute ventilation is not to be inferred.

The second sensor is preferably an accelerometer disposed within the housing of the cardiac pacemaker which generates an electronic signal proportional to the magnitude of the motion resulting from body movement. The accelerometer provides an absolute measure of activity and therefore does not require calibration such that the accelerometer may be optimized during the patient's predischarge follow up. To accomplish this, the physician may elect to have the patient undertake an extended exercise test or any of a variety of walking protocols. The electronic signal from the accelerometer may be optimized and programmed in the microprocessor of the cardiac pacemaker at fixed settings. The algorithm of the present invention will record the daily maximum pacing rates achieved based on the accelerometer. A dynamic target rate is determined by calculating the average of the maximum pacing rates achieved by the accelerometer over a predefined time period. The algorithm of the present invention thereafter automatically optimizes the physiologic sensor towards the dynamic target rate generated by the accelerometer. In this fashion, the algorithm provided in accordance with the present invention significantly reduces the time constant for optimizing the first sensor and also reduces the amount of clinical time required to initialize the cardiac pacemaker so as to boost clinical efficiency.

DESCRIPTION OF THE DRAWINGS

The foregoing features, advantages and objects will become apparent to those skilled in the art from the following detailed description of a preferred embodiment, especially when considered in conjunction with the accompanying drawings in which.

DESCRIPTION OF THE PREFERRED EMBODIMENT

Figure 1:
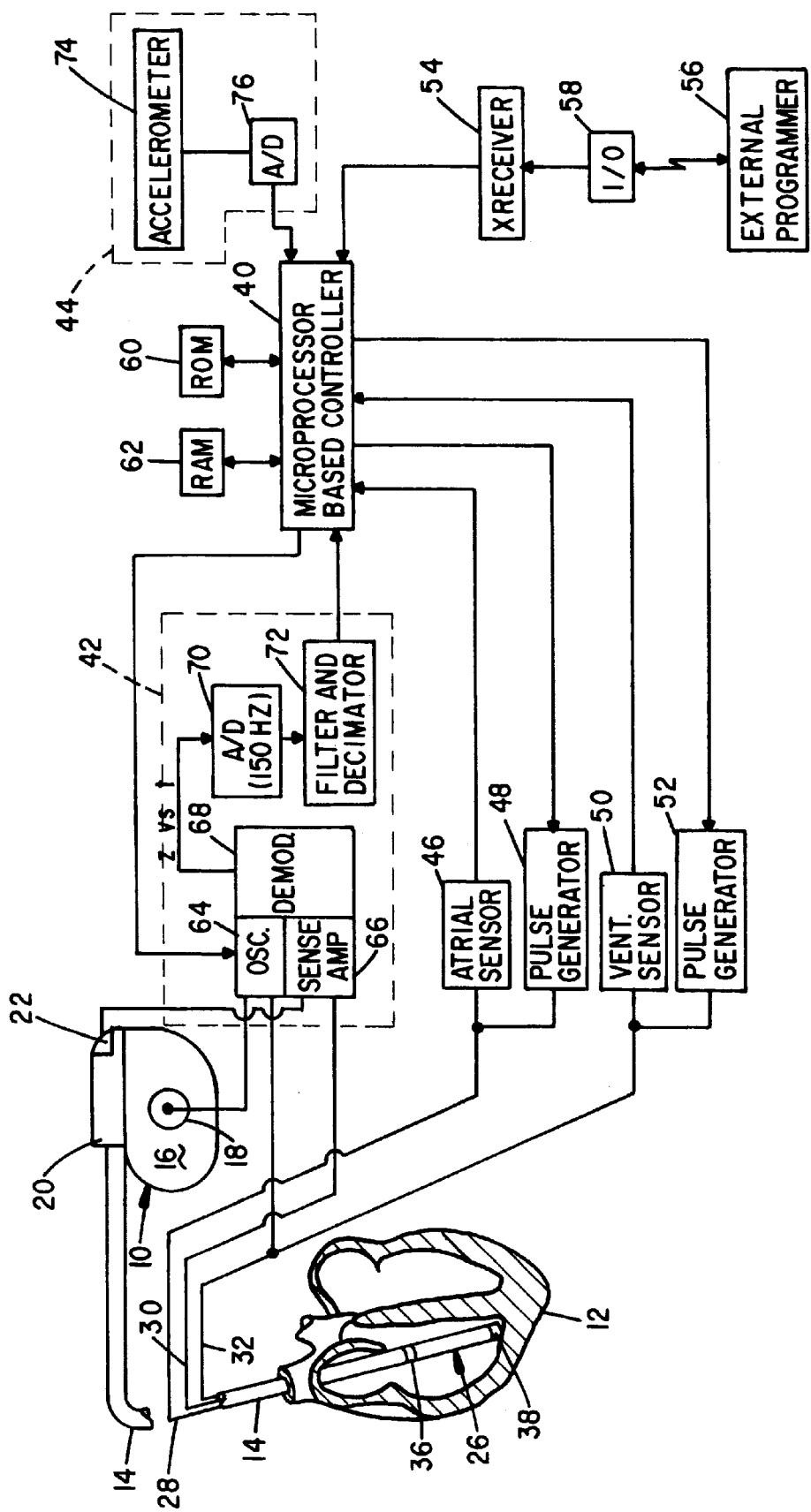
FIG. 1 is a block diagram depicting a cardiac pacemaker incorporating the automatic response optimization algorithm of the present invention.

Referring first to FIG. 1, shown in block diagram is an implantable cardiac pacemaker 10 operatively coupled to a patient's heart 12 via a pacing lead 14. By way of illustration and not limitation, the cardiac pacemaker 10 is a dual chamber (DDDR) pacer comprising a hermetically sealed container or housing 16 which is formed from metal, e.g. titanium. Extending from the top of the housing 16 is a molded plastic lead connector 20 having an indifferent metal electrode 22 disposed thereon. A pacing lead 14 extends from the lead connector 20. It is equipped with two electrodes 36, 38 with electrode 38 disposed at the distal end of the ventricular lead 14. A conductor 32 connects to the distal tip electrode 38. Electrode 36 comprises a conductive ring located proximal of the tip, but located in the right ventricle when the electrode is disposed at the apex. Conductor 30 in lead 14 connects to the ring electrode 36.

The cardiac pacemaker 10 includes a microprocessor-based controller 40 operatively coupled to a first sensor comprising a physiologic sensing circuit 42, a second sensor comprising an activity sensing circuit 44, an atrial sense amplifier 46 and pulse generator 48, a ventricular sense amplifier 50 and pulse generator 52, and a transceiver 54 for transmitting and receiving information to and from an external programmer 56 via an input/output module 58. As will be explained in greater detail below, the physiologic sensing circuit 42 is configured to detect physiologic parameters indicative of metabolic demand, while the activity sensing circuit 44 is configured to detect parameters indicative of patient movement or activity, such as during exercise. The atrial sense amplifier 46 and atrial pulse generator 48 are both operatively coupled to a tip electrode disposed at the distal end of a atrial lead, not shown via the conductor 28. The atrial sense amplifier 46 is designed to sense the occurrence of P-wave activity relating to atrial events and to forward this atrial information to the microprocessor controller 40. The atrial pulse generator 48 is designed to deliver stimulating pulses to the atrium via the tip electrode on the atrial lead not shown under the direction of the microprocessor controller 40. The ventricular sense amplifier 50 and ventricular pulse generator 52 are similarly operatively coupled to the tip electrode 38 disposed at the distal end of the ventricular lead 26 via the conductor 32. The ventricular sense amplifier 50 is equipped to sense the R-wave activity relating to ventricular depolarization and to forward this ventricular information to the microprocessor controller 40. The ventricular pulse generator 52 is designed to deliver stimulating pulses to the tip electrode 38 under the direction of the microprocessor controller 40. The cardiac pacemaker 10 also includes read-only memory (ROM) 60 and random access memory (RAM) 62 communicatively coupled to the microprocessor controller 40. The ROM 60 is used to store any of a variety of programs, including but not limited to the automatic optimization algorithm of the present invention. The RAM 62 serves as a scratchpad and active memory during execution of the programs stored in the ROM 60.

In a preferred embodiment, the physiologic sensing circuit 42 is configured to monitor the minute ventilation of the patient. It is to be readily understood, however, that minute ventilation is set forth by way of example only and that any number of different physiologic parameters indicative of metabolic demand may be employed, including but not limited to QT interval, respiration rate, venous oxygen saturation, stroke volume, PEI, dv/dt and venous blood temperature. The construction and operation of the physiologic sensing circuit 42 is disclosed in U.S. Pat. No. 5,318,598 entitled "RATE ADAPTIVE CARDIAC RHYTHM MANAGEMENT DEVICE CONTROL ALGORITHM USING TRANS-THORACIC VENTILATION, assigned to applicant's assignee, the teachings of which are hereby expressly incorporated by reference. By way of overview, the physiologic sensing circuit 42 accomplishes the desired detection of minute ventilation by providing an oscillator 64, a sense amplifier 66, a demodulator 68, an analog-to-digital (A/D) converter 70, and a filter and decimator circuit 72. The oscillator 64 is connected in driving relationship between the metal can surface 18 of the pacemaker 10 and the tip electrode 38 of the ventricular lead 26. The frequency and amplitude of the driving signal generated by the oscillator 64 is such that capture of the heart does not occur. Rather, the oscillator 64 injects a high frequency carrier signal which is modulated by respiratory activity of the patient. The oscillator 64 does not run continuously but, instead, is controlled by a wake/sleep control circuit within the microprocessor-based controller 40. The sense amplifier 66 receives the modulated respiratory signal between the indifferent electrode 22 and the ring electrode 36 disposed at the proximal end of the ventricular lead 26. The demodulator 68 receives the output of the sense amplifier 66 and serves to remove the high frequency carrier signal such that only the modulation envelope remains. The analog-to-digital (A/D) converter 70 samples the analog modulation envelope signal at a predetermined frequency and produces a serial signal train of digital pulses which define the amplitude of the analog input at the sampling time. The filter and decameter circuit 72 operates as a peak detection algorithm on the digital pulse train so as to determine tidal volume and ventilatory rate. The microprocessor-based controller 40 then operates to determine the minute ventilation as the product of the tidal volume and ventilatory rate.

In accordance with a preferred embodiment, the activity sensing circuit 44 comprises an accelerometer 74 disposed within the housing 16 of the pacemaker 10, and an analog-to-digital (A/D) converter 76 communicatively coupled to the microprocessor-based controller 40. The accelerometer 74 generates an analog signal which is representative of the level of activity experienced by the patient. The analog signal from the accelerometer 74 is transformed to a corresponding digital pulse train by the analog-to-digital converter 76 which is thereafter fed into the microprocessor-based controller 40. As will be explained in greater detail below, the microprocessor-based controller 40 generates a dynamic target rate based on the digital input derived from the accelerometer 74, wherein the dynamic target rate is used to automatically optimize the physiologic sensing circuit 42 mentioned above. Although the preferred embodiment of the activity sensing circuit 44 employs the accelerometer 74, it is to be readily understood that any of a variety of activity sensing elements may be substituted therefor, such as a piezoelectric sensor, without departing from the scope of the present invention. Having described the overall configuration of the pacemaker 10 constructed in accordance with the present invention, consideration will next be given to the operation thereof and, more particularly, to the automatic response optimization algorithms of the present invention as depicted in the software diagrams of FIGS. 2 and 3.

Figure 2:
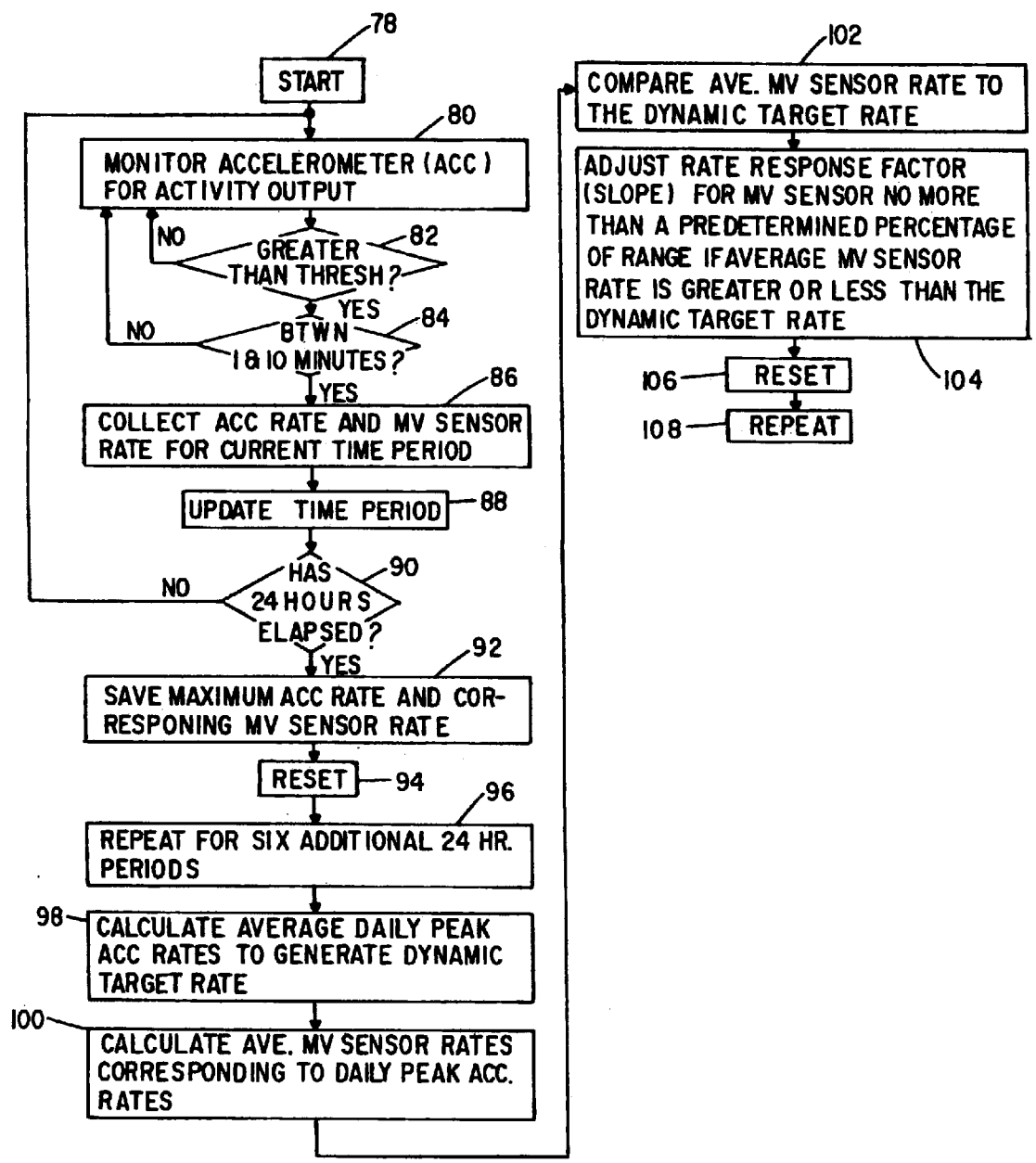
FIG. 2 is flow chart demonstrating the automatic response optimization algorithm employed by the microprocessor controller illustrated in FIG. 1 in accordance with a first preferred embodiment of the present invention.

With reference to FIG. 2, shown is a flow chart illustrating an automatic response optimization algorithm in accordance with a first preferred embodiment of the present invention. Following the start 78 of the algorithm, the first step 80 involves monitoring the output of the accelerometer to gain a continuous assessment of the physical activity of the patient. Steps 82 and 84 collectively determine whether the accelerometer is in an active state, that is, above a predetermined threshold for a predetermined period of time. In a preferred embodiment, the predetermined period of time is a range between 1 and 10 minutes. If the accelerometer sensor rate is greater than the predetermined threshold (step 82) for a length of time between 1 and 10 minutes (step 84), then the accelerometer (ACC) sensor rate and the minute ventilation (MV) sensor rate are stored in the memory of the microprocessor-based controller 40 (step 86) for that current time period. As shown in steps 88 and 90, this process is repeated over a 24 hour period such that the accelerometer sensor rate and minute ventilation sensor rate are stored in the memory of microprocessor-based controller 40 each time the accelerometer sensor rate exceeds the predetermined threshold for a length of time between 1 and 10 minutes during a 24 hour period. At the end of each 24 hour period, the maximum accelerometer sensor rate is saved in memory, along with the minute ventilation sensor rate which corresponds to the maximum accelerometer sensor rate (step 92). With the exception of the daily maximum accelerometer sensor rate and the corresponding minute ventilation sensor rate saved in step 92, all other accelerometer sensor rates and minute ventilation sensor rates recorded over the previous 24 hour period are thereafter discarded during a system reset step 94. As shown in step 96, this process is preferably repeated for, say, six additional 24 hour periods to constitute a full week in which daily maximum accelerometer sensor rates are saved along with the corresponding minute ventilation sensor rates. At the end of the seven day period, the resulting seven daily maximum or peak accelerometer sensor rates are averaged together in step 98 to generate a dynamic target rate. The resulting seven daily minute ventilation sensor rates which correspond to the daily peak accelerometer sensor rates are similarly averaged in step 100. The average of the seven daily minute ventilation sensor rates is then compared to the dynamic target rate in step 102. As shown in step 104, the rate response factor or slope of the minute ventilation sensor is adjusted no more than a small percentage of its range if the average of the seven daily minute ventilation sensor rates is greater or less than the dynamic target rate. Following the adjustment of the rate response factor of the minute ventilation sensor in step 104, the system is once again reset in step 106 and the process is repeated as indicated by step 108. It is to be understood that while the invention is explained using a week's collection of daily maximum sensor rates being collected, the collection period is arbitrary.

Figure 3:
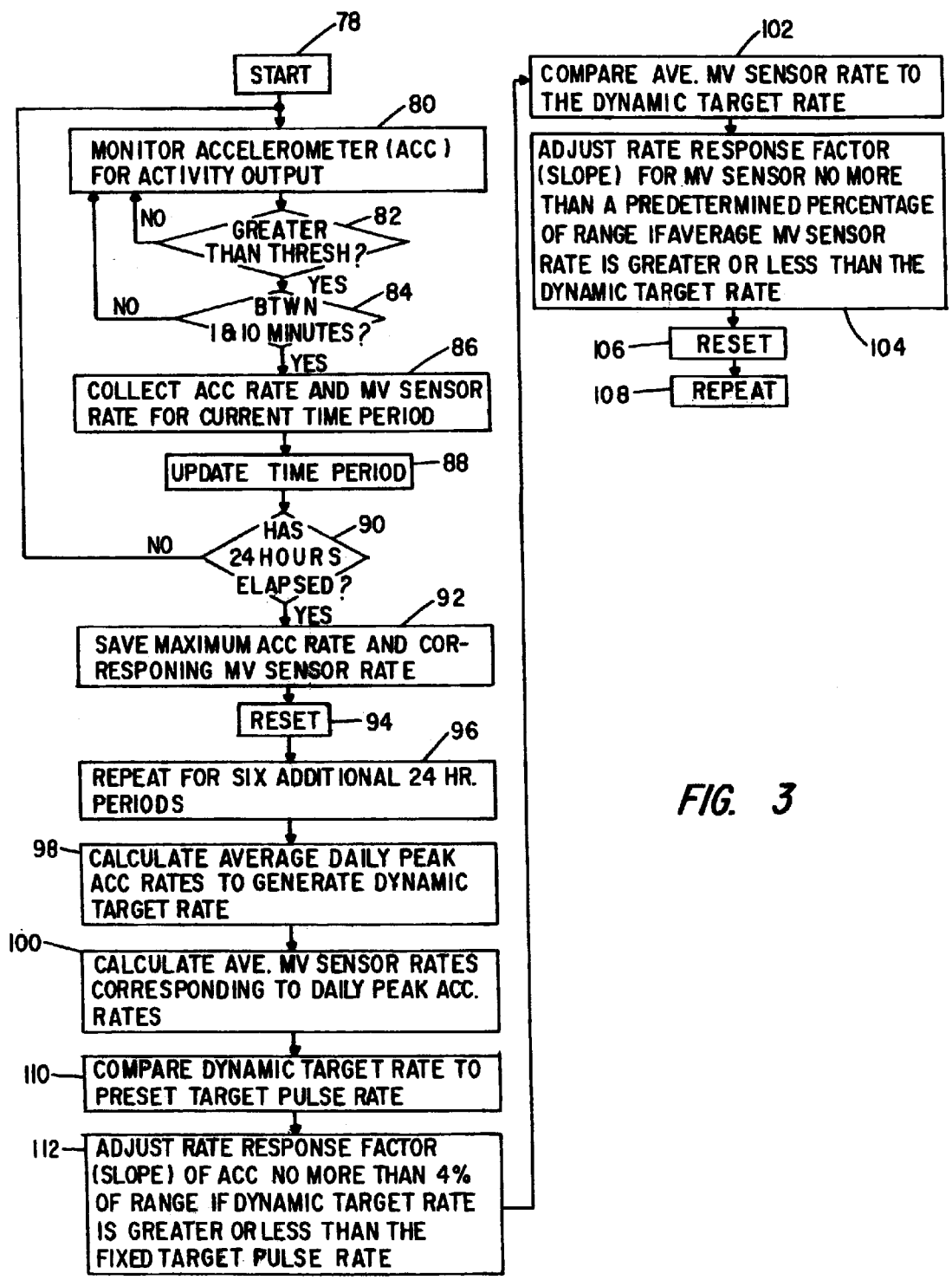
FIG. 3 is a flow chart demonstrating the automatic response optimization algorithm employed by the microprocessor controller illustrated in FIG. 1 in accordance with a second preferred embodiment of the present invention.

With reference to FIG. 3, shown is a flow chart illustrating an automatic response optimization algorithm in accordance with a second preferred embodiment of the invention. As will be readily apparent, the algorithm in FIG. 3 is based largely upon the algorithm set forth in FIG. 2 and, accordingly, a description of the steps in common will not be repeated. The main distinction is that the algorithm in FIG. 3 includes a feature to automatically optimize the response slope of the accelerometer based on a predetermined target rate as programmed by a physician. This is accomplished by simply adding steps 110 and 112 in between steps 100 and 102 of FIG. 2. More specifically, step 110 entails comparing the dynamic target rate generated in step 98 to a preset target pulse rate as programmed by a physician during a predischarge follow-up examination. The next step 112 involves adjusting the rate response factor or slope of the accelerometer if the dynamic target rate is greater or less than the predetermined target pulse rate. In a preferred embodiment, the rate response factor of the accelerometer is adjusted in the same fashion as the rate response factor of the minute ventilation sensor, that is, the rate response factor of the accelerometer will be raised or lowered no more than a predetermined percentage, e.g., 4 percent, of its range depending upon whether the dynamic target rate is lower or greater, respectively, than the fixed target rate. In this manner, then, the algorithm shown in FIG. 3 performs two separate and distinct automatic response optimization functions, namely a first wherein the rate response factor for the accelerometer is automatically optimized toward a preset target rate, and a second wherein the rate response factor for the minute ventilation sensor is automatically optimized toward the dynamic target rate.

From the foregoing, it will be appreciated that the physiologic sensor will be automatically and continuously optimized toward to the dynamic target rate. This is advantageous over the prior art implementations for several reasons. First, automatically optimizing the response rate of the physiologic sensor toward the dynamic target rate provides immediate response for the majority of exercises based on the output of the activity sensor. This advantageously allows the cardiac pacemaker to appropriately and quickly modify the pacing rate of the heart to accurately respond to changes in the patient's metabolic demand. A further advantage resides in the fact that the time constant for optimizing or adapting the physiologic sensor is dramatically shortened relative to prior art pacemakers. The algorithm exhibits a short time constant. It is optimized toward a dynamic target rate. Reducing the time constant for optimizing the slope of the output of the physiologic sensor is advantageous in that it minimizes the amount of clinical time required for the physician to effectuate the initialization of the cardiac pacemaker. As will be appreciated, this reduces the cost of conducting the initialization and effectively increases the number of patients whose pacemakers may be initialized within a given period of time so as to increase the efficiency of the clinical operations. Automatically optimizing the response slope of the physiologic sensor based on a dynamic target rate also reduces the need for physicians to manually set the response slope of the physiologic sensor in an effort to send the patients home shortly after the follow-up examination, thereby minimizing the degree to which the physiologic sensor rates are optimized based on subjective and oftentimes inaccurate "best guess" approximation.

Another advantage of the foregoing automatic response optimization algorithm is that the dynamic target rate comprises an improved feedback mechanism for adapting the response rate of the physiologic sensor. Employing the dynamic target rate as a feedback mechanism is advantageous over the prior art feedback mechanisms in that does not assume that the patient exercises up to a programmed maximum sensor rate (MSR) within a predetermined time period, thereby avoiding the inappropriate response optimization which oftentimes results from the use of such a feedback mechanism. Using the dynamic target rate as a feedback mechanism is also advantageous over prior art rate adaptive pacers in that it does not require the physician to engage in the arbitrary procedure of programming an individual patient sensor rate target (SRT) for the physiologic sensor based on highly subjective patient data. Yet another advantage of employing the dynamic target rate as the feedback mechanism is that sedentary periods will not result in an overly aggressive response for the physiologic sensor.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. More particularly, in spite of the fact that essentially both algorithms are described as a digital (microprocessor) implementation, those skilled in the art appreciate that an analog implementation and/or sampled data (switched capacitor or switched current) implementation is also possible.

What is claimed is:

1. A rate-adaptive cardiac pacemaker, comprising:
   (a) physiologic rate sensor means for sensing a physiologic parameter indicative of metabolic demand in a patient and producing an electrical signal proportional to the metabolic demand;
   (b) second sensor means for sensing a parameter indicative of patient activity and producing an electrical signal proportional to the patient's level of activity;
   (c) controller means for generating a dynamic target rate based on averages of maximum peak values of the electrical signal from said second sensor means occurring during predetermined time intervals;
   (d) optimization means for automatically optimizing a rate response factor of said physiologic rate sensor means toward said dynamic target rate by a predetermined percentage if an average physiologic sensor rate is above or below the dynamic target rate; and (e) variable rate pulse generator means for stimulating said patient's heart based on the output from said optimization means.

2. The cardiac pacemaker as set forth in claim 1 and further, said activity rate sensing second sensor means comprises an accelerometer configured to generate an analog signal corresponding to patient movement.

3. The cardiac pacemaker as set forth in claim 2 and further, said physiologic rate sensing means comprises a minute ventilation sensing circuit configured to generate an analog signal corresponding to the minute ventilation of the patient.

4. In a cardiac pacemaker of the type having pulse generating means for selectively applying stimulating pulses to cardiac tissue, the improvement comprising in combination:

(a) physiologic sensor means for sensing a physiologic parameter indicative of metabolic demand in a patient;

(b) second sensor means for sensing a parameter indicative of patient activity;

(c) controller means for generating a dynamic target rate based on the output from said second sensor means, said controller means including first detector means for detecting maximum output measurements from said second sensor means over each of a plurality of incremental periods of time occurring within a predetermined period of time, second detector means for detecting output measurements from said physiologic sensor means corresponding to each of said maximum output measurements from said second sensor means over each of said plurality of incremental periods of time within said predetermined period of time, first averaging means for producing a dynamic target rate comprising the average of said maximum output measurements from said second sensing means over said predetermined period of time, and second averaging means for generating an average physiologic sensor rate comprising the average of said output measurements from said physiologic sensor means corresponding to each of said maximum output measurements from said second sensor means over said predetermined period of time;

(d) optimization means for automatically optimizing the response rate factor of said physiologic sensor means toward said dynamic target rate, said optimization means including comparison means for comparing said average physiologic sensor rate to said dynamic target rate, and adjustment means for automatically adjusting the rate response factor of said physiologic sensor means a predetermined percentage if said average physiologic sensor rate is above or below said dynamic target rate; and (e) variable rate pulse generator means for stimulating said patient's heart based on the output from said optimization means.

5. The cardiac pacemaker as set forth in claim 4 and further, said second sensor means comprising an accelerometer configured to generate an analog signal corresponding to patient movement.

6. The cardiac pacemaker as set forth in claim 4 and further, said physiologic sensor means comprising a minute ventilation sensing circuit configured to generate an analog signal corresponding to the minute ventilation of the patient.

7. A method of automatically optimizing a rate-responsive cardiac pacemaker, comprising the steps of:

(a) providing physiologic sensor means for sensing a physiologic parameter indicative of metabolic demand in a patient;

(b) providing activity sensor means for sensing a parameter indicative of patient activity and producing a signal output proportional thereto;

(c) detecting peak values of the signal output during first predetermined time intervals;

(d) averaging the peak values at a given time interval to generate a dynamic target rate; and (e) automatically adjusting the rate response factor of said physiologic sensor means based on said dynamic target rate.

(e) automatically adjusting the rate response factor of said physiologic sensor means by a predetermined percentage based on said dynamic target rate.

* * * * *